United States Patent [19]

Wright

[11] Patent Number: 5,025,656

[45] Date of Patent: Jun. 25, 1991

[54] DENSITOMETER

[75] Inventor: Hubert A. Wright, Arlington, Mass.

[73] Assignee: Cambridge Applied Systems, Inc., Cambridge, Mass.

[21] Appl. No.: 526,128

[22] Filed: May 21, 1990

[51] Int. Cl.⁵ .................. G01N 9/10; G01N 11/10
[52] U.S. Cl. ............................ 73/32 A; 73/54; 73/57
[58] Field of Search ................. 73/32 A, 54, 57

[56] References Cited

U.S. PATENT DOCUMENTS 3,677,070 7/1972 Norcross ............................. 73/57
4,627,272 12/1986 Wright ............................... 73/57
4,864,849 9/1989 Wright ............................... 73/57

FOREIGN PATENT DOCUMENTS 1300333 3/1987 U.S.S.R. ............................ 73/57

Primary Examiner—Hezron E. Williams
Assistant Examiner—Craig Miller
Attorney, Agent, or Firm—Nutter, McClennen & Fish

[57] ABSTRACT

A densitometer (10) provides a chamber (24) within which a ferromagnetic bob (27) is shuttled back and forth by alternate driving of two coils (32 and 34). Measurement circuitry (FIG. 2) determines the density of the fluid inside the chamber (24) by comparing the stroke times in opposite directions.

13 Claims, 4 Drawing Sheets

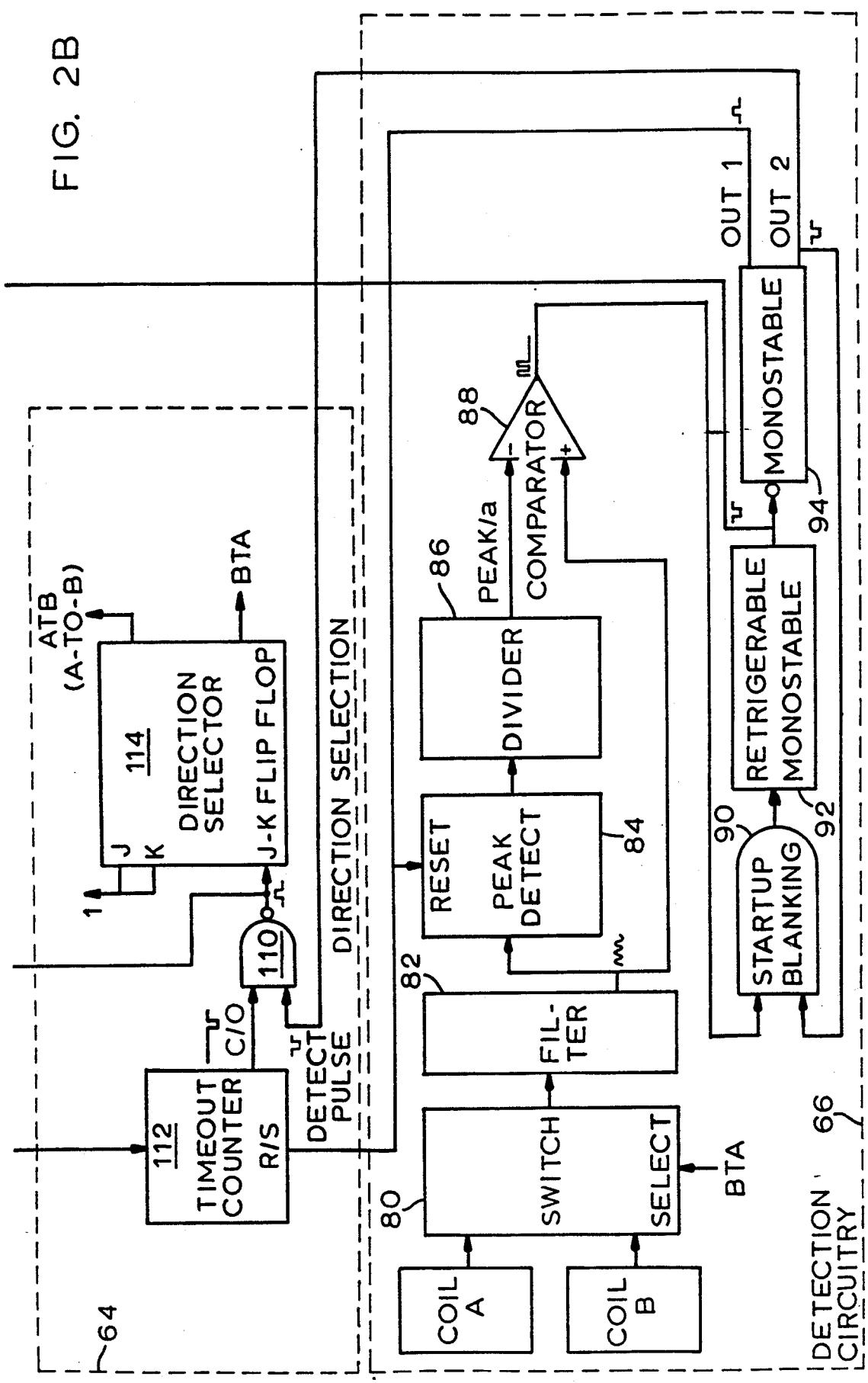

DENSITOMETER

BACKGROUND OF THE INVENTION

The present invention is directed to measurement of density, and in particular to the measurement of the density of a fluid. It is particularly beneficial in industrial applications in which simplicity is desirable and space limitations may be a factor.

Many approaches to measuring fluid density have been proposed and used. One approach that is relatively elegant from a theoretical standpoint is the one described in Soviet Inventors' Certificate No. 1,300,333. That densitometer employs a magnetic bob disposed in a chamber that has piezoelectric sensors at its upper and lower walls. An electric coil draws the ball to the top of the chamber, where the time of its arrival is sensed by the piezoelectric sensor, and the ball is then allowed to drop to the bottom of the chamber, where its arrival is similarly sensed. The current that drives the coil is adjusted so that the time required to reach the top of the chamber equals that required to reach the bottom, and computation circuitry infers the fluid density from the ratio between that current level and the current level similarly arrived at with a fluid of known density. This approach is more suited to laboratory work than to process-control applications, however, since it is relatively slow; it requires many transits through the fluid in order to arrive at the current level that will make the up and down transit times equal.

An approach with more process-control applicability is one in which radiation from a radioactive substance is directed through the fluid sample, and the proportion of the emitted radiation that passes through the fluid sample is taken as an indication of the fluid density. This approach is particularly insensitive to external vibration, but it requires both safety training of personnel and the ability to deal with any resulting health and safety problems.

Another approach employs a plummet that is designed to be positively buoyant with respect to the fluid to be measured. Chains having negative buoyancy are connected between the plummet and reference points in a chamber that contains the fluid; that is, the chamber wall supports each chain at one end, while the other end of each chain is supported by the plummet, which in turn is held down by the weight of the chain. The level at which the plummet end of the chain is held with respect to the level at which it is held by the chamber determines the distribution of the chain weight between the plummet and the chamber wall, and this in turn is determined by the buoyancy of the plummet. Consequently, the density of the fluid can be determined by the height of the plummet. This arrangement has the advantage of simplicity, but it must be made physically large to achieve adequate resistance to vibration, flow effects, and the effects of static friction, which can detract from repeatability and accuracy.

In one of the more widely used approaches, the fluid to be measured flows through a tube, which is caused to vibrate at the natural frequency that results from the tube material, its dimensions, and the fluid that it contains, i.e., the fluid to be measured. The natural frequency depends on the fluid density, which can accordingly be determined by measuring the frequency of the tube vibrations. Such an arrangement is simple in principle, and the accuracy and repeatability reported for such instruments have been good.

SUMMARY OF THE INVENTION

The densitometer of the present invention is distinguished from these prior-art densitometers in, among other things, its versatility. Like these prior-art devices, that of the present invention makes measurements from which the density of a fluid can be obtained. However, its measurements can be employed to determine not only density but also viscosity, so it can eliminate the need for a second instrument in those applications in which density and viscosity are both variables of interest.

Like the arrangement described in connection with the Soviet Inventors' Certificate mentioned above, the densitometer of the present invention employs a bob that is caused to move alternately in opposite directions along a path through the fluid to be measured. However, the present invention can employ hardware similar to that described in U.S. Pat. No. 4,864,849, which issued on Sept. 12, 1989, to Hubert A. Wright for a Viscometer. The Wright viscometer magnetically drives a bob in opposite directions to cause it to move back and forth along a predetermined path through the fluid to be measured. In that arrangement, the sum of the transit times was taken to be an indication of the viscosity of the fluid through which the bob traveled.

According to the present invention, it is the difference between the two transit times that is determined, and the density of the fluid is inferred from a function of this difference. If the instrument is to be employed in a feedback loop in which the intent is to maintain the density of the fluid at a value equal to that of the bob, it is simply the difference itself that provides the necessary indication. A positive difference means that the density needs to be changed in one direction, and a negative difference means that it should be changed in the other direction. The size of the difference can be employed to provide proportional control even though it does not alone give the actual density value. This approach can be employed even when the desired fluid density does not equal the bob density; an imbalance can be introduced in the coil currents so that the two travel times are equal when the fluid has the desired density. For density measurements to be used for other purposes, the time difference is typically divided by the total time to provide an indication of the density.

This arrangement can use the same hardware—and, indeed, the same measurements—to determine both density and viscosity at the same time. This eliminates the expense and space requirements of a separate viscometer. Additionally, the densitometer of the present invention can be made relatively insensitive to vibration; in the feedback arrangement described above, the fluid density is controlled to keep it at a level at which the bob is neutrally buoyant, so vibration of the instrument does not cause the bob to move with respect to the fluid.

BRIEF DESCRIPTION OF THE DRAWINGS

These and further features and advantages of the present invention are described in connection with the accompanying drawings, in which:

FIGS. 2A and 2B together are a block diagram of the circuitry for driving the densitometer coils, sensing bob position, measuring travel time, and generating a density indication therefrom.

DETAILED DESCRIPTION OF ILLUSTRATIVE EMBODIMENTS

Figure 1:
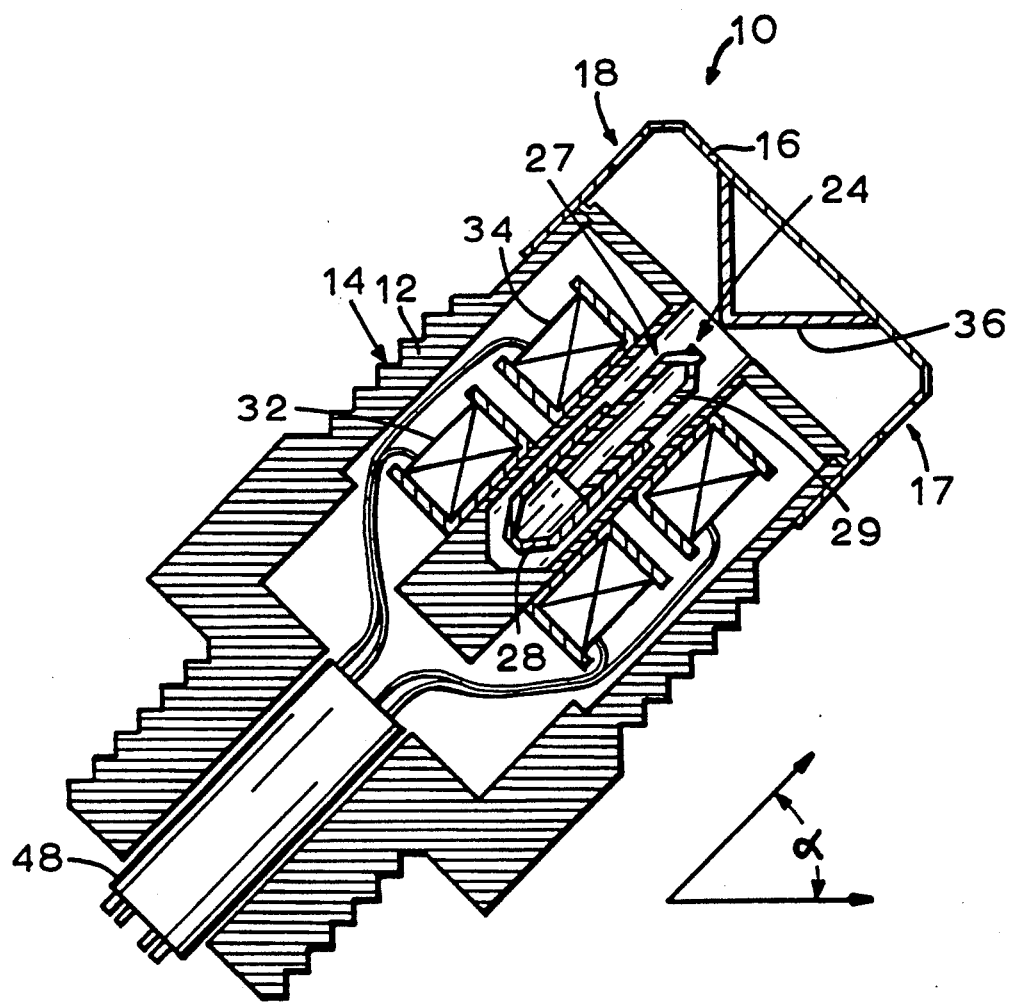
FIG. 1 is a cross-sectional view of the mechanical part of a densitometer that employs the teachings of the present invention.

FIG. 1 depicts in cross section the mechanical part 10 of a combined densitometer/viscometer that embodies the teachings of the present invention. It includes a generally cylindrical body 12 provided circumferentially with screw threads 14 intended to mate with corresponding threads in the wall of a pipe carrying the fluid whose viscosity is to be measured. In use, the shell is oriented with its axis vertical or at some angle $\alpha$ with the horizontal that results in a vertical component. An end cap 16 secured to the end of the body 12 includes openings 17 and 18 that allow fluid in which the instrument is disposed to enter and leave the device interior.

Disposed inside a chamber 24 formed inside the body is a bob 27 for which the chamber wall serves as a guide. The bob comprises two bob halves 28 and 29 welded together to give the bob a fluid-tight interior. At least one of the bob halves is made of a material whose magnetic permeability is relatively high, such as one of the 400 series (i.e., predominantly martensitic) stainless steels. Two coils 32 and 34 are disposed about the chamber wall and spaced along it. The coils are so disposed that they set up magnetic fields inside the chamber 24 when they are driven with electric current. By driving coils 32 and 34 alternately, it is possible to cause the bob 27 to reciprocate in the chamber 24. As it reciprocates, a conical baffle 36 on the end cap 16 affects fluid flow in such a manner as to aid in refreshing the contents of the chamber 24.

The piston, being made of high-permeability material, affects the mutual inductance between coils 32 and 34, so bob position can be monitored by sensing this mutual inductance. If the orientation of the bob path has a vertical component, the time required for a bob stroke depends on the relative densities of the bob and the fluid, so the fluid density can ultimately be inferred from mutual-inductance observations. In accordance with the present invention, the density is determined from the difference between the durations of travel in opposite directions.

Specifically, the time required for a bob stroke from a point A on the left to a point B on the right under a constant magnetic force if inertial and non-Newtonian viscous effects are negligible is:

$$T_{ATB} = L\sigma/kM \{1/[1-(S\sin\alpha)/M]\}, \quad (1)$$

where
 $T_{ATB}$ = travel time from point A to point B;
 L = distance from point A to point B;
 $\sigma$ = fluid viscosity;
 k = a proportionality constant that depends mainly on the size and shape of the bob;
 M = magnetic force;
 S = bob weight minus bob buoyant force, i.e., submerged weight; and
 $\alpha$ = the angle that the bob path forms with the horizontal.

The time $T_{BTA}$ required for travel in the other direction is given by the following equation:

$$T_{BTA} = (L\sigma/kM)\{1/[1+(S\sin\alpha)/M]\}. \quad (2)$$

Manipulation of equations (1) and (2) yields $$(T_{ATB}-T_{BTA})/(T_{ATB}+T_{BTA}) = (S\sin\alpha)/M \quad (3)$$

The submerged weight S is given by $$S = gV(d_b-d_f), \quad (4)$$

where:
 g = the acceleration of gravity;
 V = bob volume;
 $d_b$ = average bob density; i.e., its bob mass divided by bob volume; and
 $d_f$ = fluid density.

Substitution of (4) into (3) yields $$d_f = d_b - M(T_{ATB}-T_{BTA})/(T_{ATB}+T_{BTA})gV\sin\alpha. \quad (5)$$

Thus, by knowing the angle of the path, the density and volume of the bob, and the magnetic force that it experiences, one can determine the fluid density from time measurements in the two directions.

Moreover, inspection of equation (5) reveals that the time-measurement difference can be used in an even simpler manner in some circumstances. For instance, suppose that fluid density is used as the feedback variable in a system for controlling the amount of thinner added to a paint stream in an automated painting process. One can employ a bob whose density equals the target density and then control the process by simply increasing or decreasing the rate of thinner addition in accordance with whether the time difference is positive or negative. In such an arrangement, no calibration is necessary for the path angle, magnetic force, or bob volume, which affect only loop gain. It is also in such an arrangement that the vibration insensitivity of the present invention is greatest, since the control system keeps the bob in a neutral-buoyancy state. Alternatively, if for practical reasons the bob density does not exactly equal the desired density, the ratio of currents supplied to coils 32 and 34 can be altered so as to achieve zero time difference when the fluid is at its desired density. This alternative introduces some sensitivity to viscosity, but it can be a convenient approach when such effects can be tolerated.

Figure 2A:
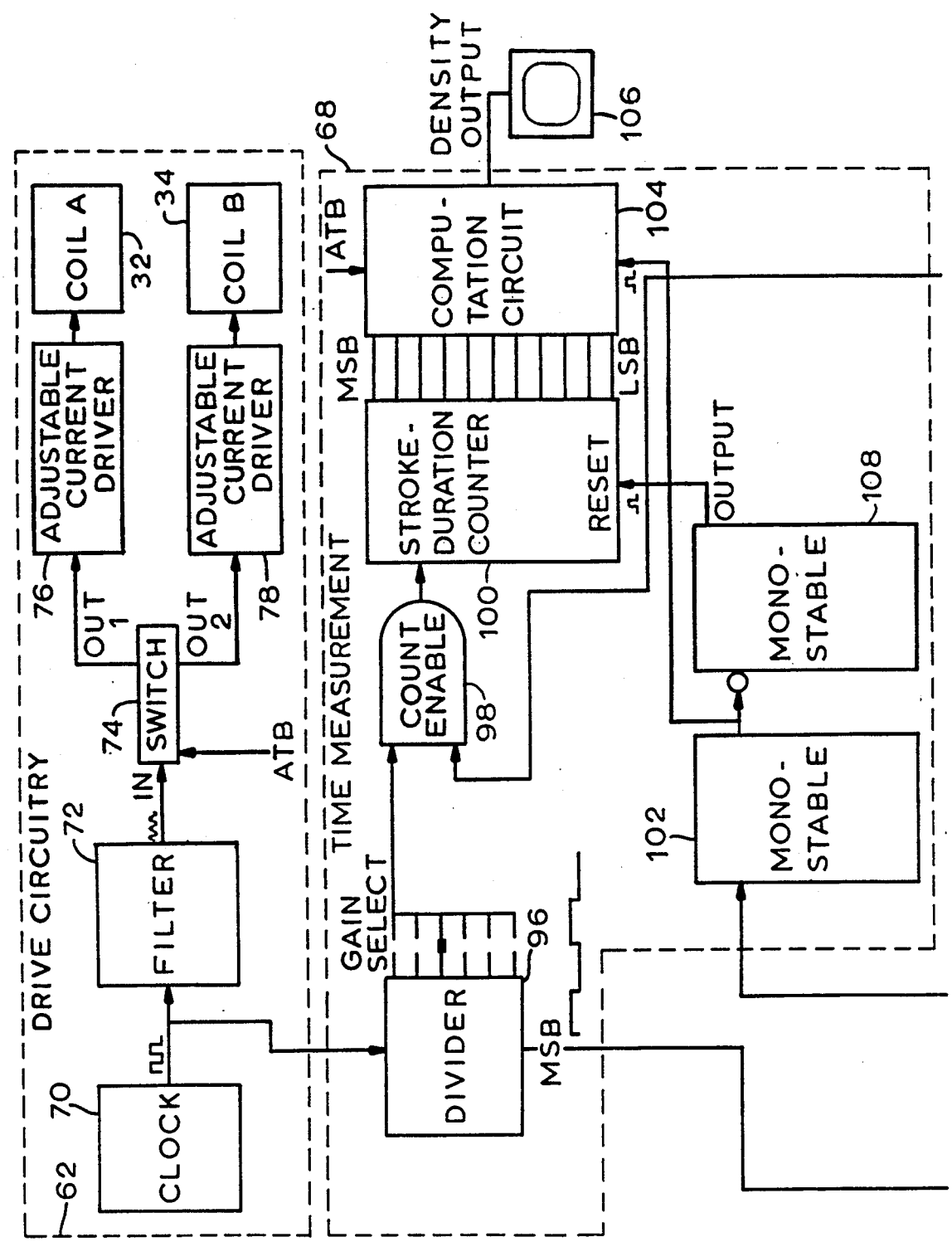

The coils 32 and 34 are connected to a cable 48, which connects it to drive and sensing circuitry depicted in FIGS. 2A and 2B. That circuitry includes a drive circuit 62 for alternately driving coils 32 and 34. The drive circuit 62 responds to an ATB signal, generated by direction-selection circuitry 64, which indicates the direction in which the drive circuit 67 is to drive the bob 27. The direction-selection circuitry 64 responds in turn to detection circuitry 66, which monitors the mutual inductance between the coils 32 and 34 so as to determine when the bob 27 has reached either end of its travel. The output of the detection circuitry 66 is also employed by a time-measurement circuit 68, which measures the duration of each stroke and generates a density indication from it.

The drive circuitry 62 includes a clock 70, which produces a periodic output. In the illustrated embodiment, the periodic output is a square wave, but other waveforms, such as triangular or sinusoidal waves, could be employed instead. A low-pass filter 72 removes the higher-frequency components from the square wave and produces an output comprising a DC level with an approximately sinusoidal AC component superimposed. The purpose of the DC component is to provide the main drive current for the coils 32 and 34, while the purpose of the AC component is to cause current flowing in one coil to induce an electromotive force in the other so that the mutual inductance between the coils 32 and 34 can be monitored.

A switch 74 responds to the ATB signal to select the coil to which the switch 74 is to forward the output of the filter 72. The switch 74 forwards its output to one or the other of two current drivers 76 and 78, which drive coils 32 and 34, respectively. The ATB signal switches between high and low levels, and the coils 32 and 34 are alternately driven as a result; when coil 32 is being driven, coil 34 is not, and vice versa. The drivers 76 and 78 are high-output-impedance circuits that produce currents whose magnitudes are determined by the voltages at their input ports and are not greatly affected by impedance changes in the coils 32 and 34 or by resistance changes in cable 48. The transconductances of drivers 76 and 78 are depicted as individually adjustable to enable the transit-time differences to be nulled. This capability may be used for initial calibration to insure that the transit time is the same in both directions for a neutrally buoyant bob despite minor mechanical asymmetries. It may also be used to unbalance the magnetic force intentionally so as to null the transit-time difference in feedback applications in which the intended density differs from the bob density.

The complement of the ATB signal is a BTA signal, which the direction-selection circuitry 64 applies to a switch 80 in the detection circuitry 66. The two inputs of switch 80 are the voltages across coils 32 and 34, and switch 80 selects one of these inputs, in accordance with the BTA signal, to apply to a filter 82 the signal that the driven coil induces in the non-driven coil. Filter 82 is a band-pass filter that increases the signal-to-noise ratio of the system by passing only the fixed fundamental frequency of the clock 70. Filter 82 feeds its output to the remainder of the detection circuitry 66. The purpose of this circuitry is to determine when the bob 27 has reached a predetermined point in each direction of travel.

When the bob 27 begins its left-to-right stroke, the mutual inductance between coils 32 and 34 is relatively low. As it moves to the right, the magnetic coupling between the coils increases until the mutual inductance reaches a maximum when the bob 27 is somewhere near the middle of its travel, after which continued travel to the right reduces the mutual inductance. The detection circuitry of FIG. 2 detects the point at which the bob 27 has reached a predetermined position toward the end of its rightward travel by determining when the mutual inductance has fallen to a predetermined percentage of the peak mutual inductance. It does this by determining when the amplitude of the AC signal on the non-driven coil falls to a predetermined percentage of its peak amplitude.

Specifically, the filter 82 applies its output to a peak detector 84, which retains as its output the highest instantaneous voltage that it has received from filter 82 since the time, at the beginning of the stroke, at which the peak detector 84 was last reset. A voltage divider 86 receives the peak-detector output and in turn produces an output that is, say, 90% of the peak output of peak detector 84. A comparator 88 subtracts this 90-per-cent-peak signal from the filter output, and the comparator 88 therefore produces a rectangular wave so long as the magnitude of the filter output remains at least 90% of the highest magnitude that it previously attained during the current stroke. That is, the comparator output remains a rectangular wave as the mutual inductance increases with rightward travel, and the rectangular wave continues after the inductance has peaked until it falls to 90% of its peak value. At that point, the rectangular wave ceases, its absence indicating that the predetermined position has been reached.

A gate 90 forwards the comparator output to a retriggerable monostable multivibrator 92 whose purpose is to indicate whether the rectangular wave is present; i.e., its output must stay high between triggerings by the low-to-high transitions of the comparator output, but it must eventually go low when the rectangular wave ceases. Accordingly, its period is greater than the clock period and thus greater than the period of the rectangular-wave output of the comparator 88.

In practice, it is preferable for the period of monostable multivibrator 92 to be at least several clock periods, because this makes the detection circuitry relatively immune to noise that might cause a pulse to be missing from the output of comparator 88. The absence of such a pulse would otherwise cause the direction to be switched prematurely.

So long as the rectangular wave is present, the monostable multivibrator 92 never returns to its stable state. But when the bob 27 reaches the predetermined position and the rectangular wave ceases, the triggering of the monostable multivibrator 92 stops, and its output accordingly goes low after its characteristic delay. As will be explained below, this low-going edge stops the timing of the current bob stroke. It also triggers a second monostable multivibrator 94, and the leading edge of the resultant pulse in the upper output of monostable multivibrator 94 resets the peak detector so that its output goes to zero and can be used on the return stroke to detect the other 90% position. The leading edge in the complementary, lower output causes an immediate change in the states of switches 74 and 80, thereby causing the coil selection for both driving and sensing to be reversed, as will be described presently. The bob driving force thus reverses immediately after timing of the last stroke stops.

Monostable multivibrator 94 has a period that will be assumed to be, for purposes of explanation, twice that of monostable multivibrator 92. For that length of time, the lower output of monostable multivibrator 94 disables gate 90. As will be explained below, this compensates for errors that would otherwise result from the delay between the actual end of the rectangular wave and the time at which monostable multivibrator 92 produces the resulting end-of-stroke indication.

To time a bob stroke, a digital divider 96 in the time-measurement circuit 68 receives the output of the clock 70 and produces a square wave that has a period equal to an integral number of clock periods. So long as the output of monostable multivibrator 92 is high, an AND gate 98 forwards the divider output to a counter 100, whose purpose is to time the bob travel. That is, the AND gate 98 forwards the count pulses as the bob 26 travels to the 90% point, and it continues forwarding pulses after the bob passes the 90% point until monostable multivibrator 92, which the comparator output no longer triggers after the 90% point is reached, times out and generates a low output. This output disables gate 98, and counter 100 stops receiving pulses.

Figure 3A:
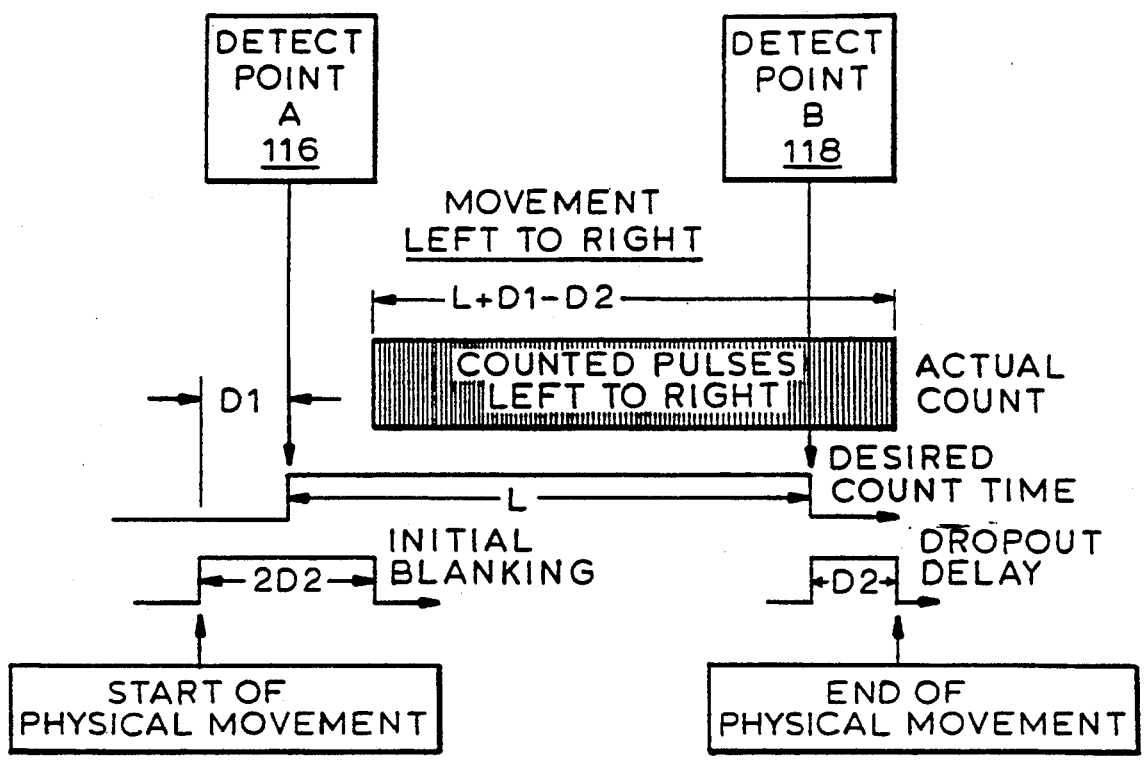
FIGS. 3A and 3B are diagrams illustrating bob travel and the parts of that travel during which the circuitry measures time.

As will be explained in more detail below in connection with FIGS. 3A and 3B, this means that, although the densitometer works on the principle of measuring the travel time for a known distance, the part of each bob stroke that the time-measurement circuit 64 times is not, strictly speaking, a fixed distance; the time-measurement circuit 64 measures the time required for the bob to arrive at the point that it reaches when it has traveled beyond the 90% point for one period of monostable multivibrator 92. As will become apparent, however, this departure from a fixed distance can be made arbitrarily small to meet the required accuracy, so the distance through which travel time is measured can be considered a fixed value.

After counter 100 stops receiving pulses, another monostable multivibrator 102 generates a pulse, as will be explained below, whose leading edge causes a computation circuit 104, typically in the form of a microprocessor, memory, and related I/O circuits, to read the counter output. The computation circuit also receives an ATB signal, which indicates whether the measurement that it has read represents the transit time from A to B or that from B to A, as will be explained below.

It can be appreciated that the output of the counter 100 for a given transit time depends on the setting of programmable divider 96. Accordingly, divider 96 can be used as a gain selector.

After the leading edge of a monostable-multivibrator-102 pulse causes the computation circuit 104 to read the contents of counter 100, the trailing edge of that pulse triggers another monostable multivibrator 108, whose resultant output resets counter 100 so that it can begin a new count.

With the measurement of the A-to-B stroke completed, the circuitry turns to the B-to-A measurement. The direction-selection circuitry 64 receives as one input of a NAND gate 110 the lower output of monostable multivibrator 94, which, as was mentioned above, was triggered when the mutual inductance fell to below 90% of its peak value. The other input of NAND gate 110 is the output of a time-out counter 112, whose function will be described below but whose output can be assumed to be high ordinarily. Accordingly, the output of NAND gate 110 is usually low, but it goes high on the falling leading edge of the output of monostable multivibrator 92, which signals the end of a bob stroke. The rising leading edge of the gate-110 output is what causes monostable multivibrator 102 to trigger the latching of the stroke duration from counter 100 into the computation circuit 104.

That leading edge also clocks a J-K direction-selection flip-flop 114, whose previously mentioned complementary ATB and BTA outputs represent the direction of the current stroke; i.e., they indicate whether the bob 27 is currently traveling from A to B or from B to A. The J and K input ports of flip-flop flop 114 are tied to a logic 1, so that flip-flop toggles on each clock pulse that it receives. Since the bob was previously traveling from A to B, the ATB signal was high, and receipt of the clock transition causes it to go low and BTA to go high. As was described before, this causes the drive circuit 62 to switch the coil that it drives and causes the detection circuit to switch the coil that it monitors.

Time-out counter 112 is set to produce a low-going pulse when it reaches a count that represents a predetermined time interval that is typically 20% longer than the highest expected bob-stroke duration. The upper output of monostable multivibrator 94 resets counter 112 at the end of each stroke, however, so time-out counter 112 is usually reset before its output has had a chance to go low. It is thus the detection circuitry, not the time-out counter 112, that ordinarily toggles the direction-selection flip-flop 114. When the system is first turned on, however, it is the time-out counter 112 that produces the first toggle pulse, and the time-out counter also produces toggle pulses to enable the system to recover if the detection circuitry 66 fails for some reason to detect the passage of the bob 26 through the detection point.

Operation of the circuitry of FIGS. 2A and 2B will be described in connection with the diagrams of FIGS. 3A and 3B, which represent the motion of the bob 27. Detect points 116 and 118 represent the two points in the travel of bob 26 at which the mutual inductance falls below 90% of its peak value and the square-wave output of the comparator 88 therefore ceases. The distance between these two points will be assumed to be L, and the densitometer operates, in principle, by measuring the time required to traverse that distance. The teachings of the present invention can thus be practiced in embodiments in which the time measurement stops as soon as the bob reaches the detect point 116. Because of the manner in which the illustrated embodiment determines that the square wave has stopped, however, counter 100 does not stop counting immediately when the bob 26 r Ⓡaches a detect point 116 or 118.

Specifically, when the bob passes to the left (in the B-to-A direction) through 90% point 116, the square wave produced by comparator 88 stops, so triggering of monostable multivibrator 92 does, too. The stroke-duration counter 100 keeps receiving count signals, however, and thus keeps incrementing. It is only when the period of monostable multivibrator 92 has passed without any more pulses from comparator that the circuit concludes that the rectangular wave has stopped, and it is then that the low-going output of monostable multivibrator 92 disables AND gate 98 so that the stroke-duration counter stops receiving pulses and thus stops incrementing. The same signal transition in the output of monostable multivibrator 92 triggers monostable multivibrator 94, thereby causing the coil drive to switch, as was described above. Also, since the B-to-A stroke has just ended, the computation circuit 104 reads the output of counter 100, which is then reset after the time-out period of monostable multivibrator 108.

In the time required for monostable multivibrator 92 to time out and thus cause the drive circuit to switch coils, the bob 26 has passed beyond point 116 by a distance $D_1$. Therefore, the bob begins its A-to-B (left-to-right) stroke from a point $D_1$ beyond point 116, as FIG. 4A indicates. The time measurement does not begin at that point, however. The count-enable gate 98, which forwards count signals to the stroke-duration counter 104, remains disabled because the retriggerable monostable multivibrator 92, which must be triggered in order to enable gate 98, initially receives no trigger signals. Although the triggering of monostable multivibrator 94 has caused it to reset the peak detector 84 so that comparator 88 produces the rectangular wave that ordinarily triggers the retriggerable monostable multivibrator 94, the blanking gate 90 does not initially forward the rectangular wave to the retriggerable monostable multivibrator 92, because gate 90 is disabled when monostable multivibrator 94 is in its unstable state.

The period of monostable multivibrator 94 is twice that of monostable multivibrator 92, so the duration of the interval during which the lower output of monostable multivibrator 94 disables gate 90—and ultimately prevents pulses from reaching the (now-reset) counter 100—is twice that during which the bob traveled through distance $D_1$. In this length of time, the bob travels a distance $2D_2$ back to the right, as FIG. 3A indicates, and counter 100 receives no count pulses during that part of bob travel. Accordingly, time measurement does not begin until the bob has reached a distance $2D_2-D_1$ to the right of point 116.

Counting then begins and continues until the bob reaches a point $D_2$ to the right of point 118, at which time monostable multivibrator 92 again times out and stops counter 100, and the computation circuit again reads the output of the stroke-duration counter, which is again reset. The computation circuit 104 has thus read a count that represents the time that has been required for the bob to travel a distance equal to $L+D_2-(2D_2-D_1)=L+D_1-D_2$, as FIG. 3A indicates.

Figure 3B:
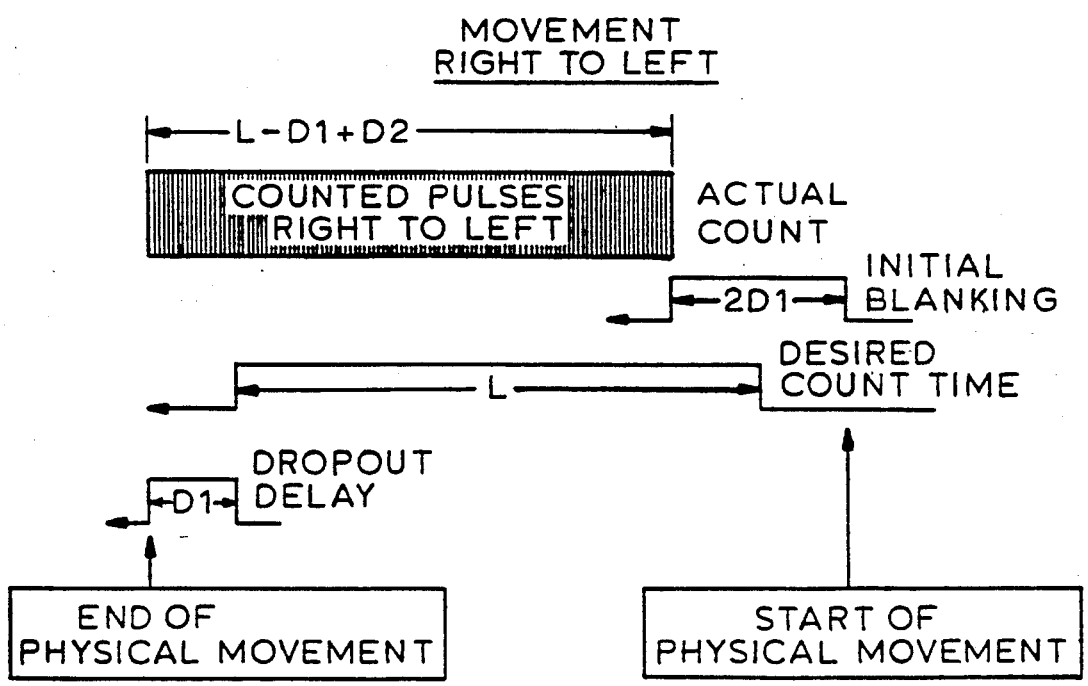

FIG. 3B depicts the B-to-A stroke and indicates that the counter 100 begins timing that stroke when the bob reaches a point $2D_1-D_2$ to the left of detect point 118. Timing continues until the bob reaches a point disposed a distance $D_1$ to the left of detect point 116. The counter 110 thus counts the time required for the bob to travel a distance $L+D_1-(2D_1-D_2)=L-D_1+D_2$. Accordingly, both distances that the circuitry has measured differ from L by $D_1-D_2$. An appropriate choice of the drive-signal frequency and thus of the periods of monostable multivibrator 92 and 94 can make this distance very small in comparison with L, however, so the accuracy penalty exacted by the operation of those monostable multivibrators can be kept small.

The measurements having been made, the computation circuit 104 proceeds to compute the fluid density in accordance with the equation (5) and display the result on an appropriate display device 106. In principle, the calculation is straightforward, since equation (5) consists only of two variables, $T_{ATB}$ and $T_{BTA}$. The angle $\alpha$, the volume V of the bob, and the acceleration g of gravity are all simple to determine. The magnetic force M used in the equation, however, is an effective value, the real value of magnetic force typically showing some variation during the stroke. To determine the value of M, therefore, a calibration step is performed. In some cases it may be desirable to perform a separate calibration operation for each individual instrument, but a common calibration for all copies of each model is adequate if sufficient manufacturing uniformity is maintained. The calibration would simply be performed by taking measurements on a fluid of known density and solving equation (5) for M, i.e., calculating M in accordance with the following equation:

$$M = gV\sin\alpha(d_b - d_f)(T_{ATB} + T_{BTA})/(T_{ATB} - T_{BTA}). \tag{6}$$

This value of effective magnetic force is then used in the actual measurement calculations.

As was mentioned above, it is possible to employ the same time measurements to determine the viscosity of the liquid as well as its density. Manipulation of equations (1) and (2) results in the following expression for the viscosity $\sigma$:

$$\sigma = (T_{ATB} + T_{BTA})[1 - (S^2/M^2)\sin^2\alpha]kM/2L. \tag{7}$$

A perusal of equation (7) reveals that all of the constants except for the effective magnetic force M and proportionality constant k are readily determined. The determination of the effective magnetic force M was just explained, and the constant k can also be determined in an appropriate calibration step. Specifically, the proportionality constant k can be determined by taking the time measurements for a fluid of known viscosity and solving equation (7) for k. That is, $$k = (2L\sigma)/M(T_{ATB} + T_{BTA})[1 - s^2/M^2)\sin^2\alpha]$$

With this value of the proportionality constant, equation (7) can be used to determine the viscosities of unknown fluids.

Review of the equations above reveals that they are based on the tacit assumption that the time required for the bob to reach its terminal velocity is negligible. For relatively inviscid fluids, however, this assumption does not accurately approximate reality, so the accuracy of the instrument tends to deteriorate after viscosity falls below a certain level. To increase the viscosity range throughout which the device is usable, one can adjust the length of the initial blanking interval set by monostable multivibrator 94.

The theory behind the adjustment can be understood by recognizing that the analysis set forth above, which indicated that the bob travel during the initial blanking was $2D_2$, i.e., twice the dropout delay $D_2$ encountered at the other end of the stroke, was based on the assumption that the bob instantaneously changes direction and assumes its terminal velocity. Of course, this assumption is not strictly true, but it is a reasonable approximation for most operating conditions. As fluids become more inviscid, however, the approximation becomes less accurate, because the velocities involved are greater, and the difference between the initial blanking-time travel and $2D_2$ becomes significant as a fraction of $2D_2$. Moreover, since the distances $D_1$ and $D_2$ also become greater in comparison with the stroke L that the instrument is to time, the errors introduced by inertial effects can become significant. As was stated above, the $D_1$ and $D_2$ distances can be made arbitrarily small by increasing the drive-current frequency, but this does not reduce the magnitude of the inertia-induced inaccuracies that become significant at the higher bob velocities that occur in less-viscous fluids.

In order to extend the range of accuracy of the device, it is initially calibrated as described above by using a relatively viscous calibrating fluid. In the initial calibration, the blanking period of monostable multivibrator 94 is equal to twice that of the end-of-stroke-detection monostable multivibrator 92. A further step is then performed with a relatively inviscid fluid. In this step, the parameters M and k determined in the initial calibration are employed to measure the viscosity of a known fluid whose viscosity is near the lower end of the extended range, and the error between the measured value and the known value is observed. The period of monostable multivibrator 94 is then adjusted upward from twice that of the retriggerable monostable multivibrator 92 until the measured value equals the known value. This period is then used in subsequent measurements of unknown fluids.

This period is the one at which monostable multivibrator 94 best compensates not only for the delay of retriggerable monostable multivibrator 92 but also for inertial effects that become significant at the low, calibration viscosity level. It does not provide the proper compensation at the higher viscosity levels, but the delays introduced by monostable multivibrators 92 and 94 at those viscosity levels are relatively insignificant, since the time required for the overall stroke is much greater. By using this approach, therefore, it is possible to extend the usable viscosity range of the device considerably.

The computation circuit 104 can be provided with a calculation mode, in which it determines M and k and stores them in appropriate internal registers for regular measurement operations. Alternatively, the contents of those registers can be obtained from calibration computations performed externally. In either case, the calibration operations described above can be supplemented in further refinements of the present invention with calibration steps that determine linearizing factors by which the results of equations (5) and (7) are adjusted so as to reduce the effects of nonlinearities omitted from the theoretical discussion set forth above.

Although I have described one embodiment of the invention, its principles can be embodied in circuitry that differs significantly from that illustrated in the drawings. For a feedback arrangement in which the bob is to be maintained at neutral buoyancy, for example, the duration counter 100 can be an up/down counter that is reset only on every other stroke and has its mode determined in accordance with the state of the ATB or BTA signal. No computation would be required, and the computation circuit could be replaced with a simple latch.

It can be seen as a result of the foregoing description that the densitometer of the present invention not only is simple but also can be arranged to be relatively insensitive to vibration. Moreover, it can provide not only density measurement but also a viscosity measurement at the same time and thus eliminate the need for an expensive second instrument, and it can be practiced in a wide range of embodiments. It therefore constitutes a significant advance in the art.

What is claimed as new and desired to be secured by Letters Patent of the United States is:

1. A densitometer comprising:
A) a bob comprising ferromagnetic material:
B) guide means for guiding the bob along a bob path through a fluid whose density is to be measured;
C) bob-driving means for driving the bob alternately in opposite directions along the bob path, the bob-driving means including (i) first and second coils disposed adjacent the path for producing, when the coils conduct current, magnetic fields in the path that drive the bob in opposite directions and (ii) a current-driver circuit for alternately driving current through the first and second coils; and
D) sensing and measuring means for monitoring bob position, measuring the travel times required for the bob to travel known distances in both directions along the bob path, generating an indication of the difference between the measured times, and thereby indicating the relative density of the fluid whose density is to be measured.

2. A densitometer as defined in claim 1 wherein:
A) the first and second coils are so oriented that their mutual inductance is a function of bob position; and
B) the sensing and measuring means comprises means for monitoring the mutual inductance of the coils and measuring the travel time by measuring time intervals defined by the times at which the monitored inductance reaches points in its position function that correspond to predetermined bob positions.

3. A densitometer as defined in claim 1 wherein:
A) the current-drive circuit is responsive to coil-selecting control signals applied thereto to drive electric current through the selected coil, whereby the bob can be driven back and forth along the bob path in oppositely directed strokes;
B) the sensing and measuring means includes:
   i) a position-sensing circuit coupled to the coils for generating a comparison signal representing the comparison of (a) the instantaneous voltage induced in the non-selected coil with (b) a predetermined fraction of the peak value achieved by the induced voltage during the current bob stroke, whereby the comparison signal comprises a square wave having first- and second-direction transitions so long as the induced voltage is an AC signal whose amplitude remains above the predetermined fraction of its peak amplitude;
   ii) a delay circuit comprising:
      a) a retriggerable first monostable multivibrator having a first period and being coupled for triggering by first-direction transitions of the comparison signal; and
      b) a second monostable multivibrator having a second period greater than the first period and being coupled for triggering by transitions of the output of the first monostable multivibrator that represent resumption of the stable state of the first monostable multivibrator;
   iii) timing circuitry responsive to the delay circuitry to measure time intervals that start when the second monostable multivibrator resumes its stable state and end when the first monostable multivibrator resumes its stable state, the timing circuitry generating an indication of the measured time;
   iv) difference circuitry, responsive to the indications of measured time, to generate the indications of the difference between the measured times;
C) the bob-driving means further includes direction-control circuitry coupled to the coil driver and for application of control signals thereto and responsive to resumption by the first monostable multivibrator of its stable state to apply to the coil driver control signals that switch the coil selection by the coil driver.

4. A densitometer as defined in claim 3 wherein:
A) the densitometer includes a gate responsive to the state of the second monostable multivibrator and interposed between the position-sensing circuit and the first monostable multivibrator to prevent the first monostable multivibrator from being triggered by the comparison-signal transitions when the second monostable multivibrator is in its unstable state but to permit the first monostable multivibrator to be triggered by the comparison-signal transitions when the second monostable multivibrator is in its stable state; and B) the timing circuitry measures the time intervals during which the first monostable multivibrator is in its unstable state.

5. A densitometer as defined in claim 4 wherein the indication of the difference between the measured times represents a quantity proportional to the ratio of the difference between the measured time to their sum.

6. A densitometer as defined in claim 3 wherein the indication of the difference between the measured times represents a quantity proportional to the ratio of the difference between the measured time to their sum.

7. A densitometer as defined in claim 2 wherein the indication of the difference between the measured times represents a quantity proportional to the ratio of the difference between the measured time to their sum.

8. A densitometer as defined in claim 1 wherein the indication of the difference between the measured times represents a quantity proportional to the ratio of the difference between the measured time to their sum.

9. A densitometer as defined in claim 8 wherein the sensing and measuring means further includes means for generating an indication of the sum of the measured times and thereby indicating the viscosity of the fluid.

10. A densitometer as defined in claim 1 wherein the sensing and measuring means further includes means for generating an indication of the sum of the measured times and thereby indicating the viscosity of the fluid.

11. A densitometer as defined in claim 1 wherein the currents that the current-driver circuit drives through the first and second coils can be separately adjusted so as to null the difference between the travel times in the opposite directions through a fluid whose density differs from that of the bob.

12. For measuring the density of a fluid, a method comprising the steps of:
A) providing a bob comprising ferromagnetic material;
B) magnetically driving the bob through the fluid alternately in opposite directions along a bob path;
C) taking measurements of the travel times required for the bob to travel known distances in both directions along the bob path; and
D) generating an indication of the difference between measured times and thereby of the density of the fluid.

13. A method of measuring density comprising the steps of:
A) providing a bob that includes ferromagnetic material and is adapted to be driven back and forth along a bob path through a fluid whose density is to be measured;
B) providing first and second coils so disposed adjacent the path that their mutual inductance is a function of the position of the bob along the path;
C) driving the bob back and forth in strokes along the bob path;
D) causing an alternating current to flow in one of the coils while the bob is being driven;
E) sensing the voltage induced in the other coil and performing a comparison of (1) the instantaneous voltage induced in the non-selected coil with (2) a predetermined fraction of the peak value achieved by the induced voltage during the current bob stroke whereby the comparison changes between two values so long as the induced voltage is an AC signal whose amplitude remains above the predetermined fraction of its peak amplitude;
F) changing the direction in which the bob is driven a first period of time after the comparison has changed to a given value and remained at that value in the interim, the first period being greater than the period of the AC signal;
G) measuring time intervals that begin a second period after direction changes and ends at the subsequent direction changes, the second period being greater than the first period; and
H) generating an indication of the difference between the lengths of the measured time intervals and thus of the density of the fluid whose density is to be measured.

* * * * *